(12) United States Patent  
Schwab et al.

(10) Patent No.: US 7,998,212 B2  
(45) Date of Patent: Aug. 16, 2011

(54) TRANSFORAMINAL HYBRID IMPLANT

(75) Inventors: Frank J. Schwab, New York, NY (US); Brian Robert Thoren, Memphis, TN (US); Anthony J. Melkent, Memphis, TN (US); John L. White, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1116 days.

(21) Appl. No.: 11/527,121

(22) Filed: Sep. 26, 2006

(65) Prior Publication Data

US 2007/0093898 A1   Apr. 26, 2007

Related U.S. Application Data

(60) Provisional application No. 60/720,555, filed on Sep. 26, 2005.

(51) Int. Cl.  
A61F 2/44 (2006.01)

(52) U.S. Cl. .................................. 623/17.16; 623/17.11

(58) Field of Classification Search .................. 623/17.16  
See application file for complete search history.

(56) References Cited

U.S. PATENT DOCUMENTS

| | | |
|---|---|---|
| 5,071,437 A | 12/1991 | Steffee |
| 5,192,327 A | 3/1993 | Brantigan |
| 5,397,364 A | 3/1995 | Kozak et al. |
| 5,782,830 A | 7/1998 | Farris |
| 6,039,762 A | 3/2000 | McKay |
| 6,126,688 A | 10/2000 | McDonnell |
| 6,159,211 A | 12/2000 | Boriani et al. |
| 6,159,215 A | 12/2000 | Urbahns et al. |
| 6,241,733 B1 | 6/2001 | Nicholson et al. |
| 6,296,665 B1 | 10/2001 | Strnad et al. |
| 6,319,257 B1 | 11/2001 | Carignan et al. |
| 6,428,544 B1 | 8/2002 | Ralph et al. |
| 6,447,543 B1 | 9/2002 | Studer et al. |
| 6,461,359 B1 | 10/2002 | Tribus et al. |
| 6,478,801 B1 | 11/2002 | Ralph et al. |
| 6,527,773 B1 | 3/2003 | Lin et al. |
| 6,562,072 B1 | 5/2003 | Fuss et al. |
| 6,569,168 B2 | 5/2003 | Lin |
| 6,579,318 B2 | 6/2003 | Varga et al. |
| 6,585,749 B2 | 7/2003 | Hanson |
| 6,599,294 B2 | 7/2003 | Fuss et al. |
| 6,613,090 B2 | 9/2003 | Fuss et al. |
| 6,626,943 B2 | 9/2003 | Eberlein et al. |
| 6,645,248 B2 | 11/2003 | Casutt |
| 6,648,915 B2 | 11/2003 | Sazy |
| 6,666,866 B2 | 12/2003 | Martz et al. |
| 6,679,887 B2 | 1/2004 | Nicholson et al. |
| 6,712,819 B2 | 3/2004 | Zucherman et al. |
| 6,712,852 B1 | 3/2004 | Chung et al. |
| 6,719,794 B2 | 4/2004 | Gerber et al. |
| 6,733,504 B2 | 5/2004 | Lin et al. |

(Continued)

FOREIGN PATENT DOCUMENTS

WO    WO 00/16711 A2    3/2000

(Continued)

*Primary Examiner* — Eduardo C Robert  
*Assistant Examiner* — Ellen C Hammond

(57) ABSTRACT

An implant configured for placement through a transforaminal surgical approach made of at least two different materials. The implant may include materials with varying radiolucency and mechanical properties. Such a hybrid implant may offer controlled radiographic visibility and optimized structural properties for implant placement, including placement for use in spinal arthrodesis.

29 Claims, 14 Drawing Sheets

U.S. PATENT DOCUMENTS

| | | | |
|---|---|---|---|
| 6,746,454 | B2 | 6/2004 | Winterbottom et al. |
| 6,770,096 | B2 * | 8/2004 | Bolger et al. ............... 623/17.16 |
| 6,790,233 | B2 | 9/2004 | Brodke et al. |
| 7,037,339 | B2 * | 5/2006 | Houfburg .................... 623/17.11 |
| 7,137,997 | B2 * | 11/2006 | Paul ........................... 623/17.11 |
| 7,192,447 | B2 * | 3/2007 | Rhoda ........................ 623/17.11 |
| 7,361,193 | B2 * | 4/2008 | Frey et al. .................. 623/17.16 |
| 7,575,580 | B2 * | 8/2009 | Lim et al. ........................ 606/99 |
| 2001/0021853 | A1 | 9/2001 | Heckele et al. |
| 2002/0065558 | A1 | 5/2002 | Varga et al. |
| 2002/0065560 | A1 | 5/2002 | Varga et al. |
| 2002/0165550 | A1 | 11/2002 | Frey et al. |
| 2003/0014057 | A1 | 1/2003 | Ralph et al. |
| 2003/0014115 | A1 | 1/2003 | Ralph et al. |
| 2003/0023245 | A1 | 1/2003 | Ralph et al. |
| 2003/0083747 | A1 | 5/2003 | Winterbottom et al. |
| 2003/0105527 | A1 | 6/2003 | Bresina |
| 2003/0109928 | A1 | 6/2003 | Pasquet et al. |
| 2003/0125739 | A1 | 7/2003 | Bagga et al. |
| 2003/0130667 | A1 | 7/2003 | Lin |
| 2003/0135275 | A1 | 7/2003 | Garcia et al. |
| 2003/0139812 | A1 | 7/2003 | Garcia et al. |
| 2003/0139813 | A1 | 7/2003 | Messerli et al. |
| 2003/0149438 | A1 | 8/2003 | Nichols et al. |
| 2003/0208203 | A1 | 11/2003 | Lim et al. |
| 2004/0034430 | A1 | 2/2004 | Falahee |
| 2004/0064184 | A1 | 4/2004 | Chung et al. |
| 2004/0068318 | A1 | 4/2004 | Coates et al. |
| 2004/0082999 | A1 | 4/2004 | Mathys, Jr. et al. |
| 2004/0122518 | A1 | 6/2004 | Rhoda |
| 2004/0126407 | A1 | 7/2004 | Falahee |
| 2004/0158324 | A1 | 8/2004 | Lange |
| 2005/0027360 | A1 * | 2/2005 | Webb et al. ................. 623/17.11 |
| 2005/0038431 | A1 * | 2/2005 | Bartish et al. .................... 606/61 |
| 2005/0049706 | A1 | 3/2005 | Brodke et al. |
| 2005/0096745 | A1 | 5/2005 | Andre et al. |
| 2005/0143822 | A1 | 6/2005 | Paul |
| 2005/0177238 | A1 | 8/2005 | Khandkar et al. |
| 2005/0187625 | A1 * | 8/2005 | Wolek et al. ................ 623/17.11 |
| 2005/0251260 | A1 | 11/2005 | Gerber et al. |
| 2006/0241761 | A1 * | 10/2006 | Gately ....................... 623/17.11 |
| 2006/0264968 | A1 * | 11/2006 | Frey et al. ....................... 606/99 |
| 2007/0173820 | A1 * | 7/2007 | Trieu .............................. 606/61 |

FOREIGN PATENT DOCUMENTS

| | | |
|---|---|---|
| WO | WO 02/17823 A1 | 3/2002 |
| WO | WO 02/080823 A1 | 10/2002 |
| WO | WO 03/068111 A2 | 8/2003 |
| WO | WO 2004/071346 | 8/2004 |
| WO | WO 2005/041825 A1 | 5/2005 |

* cited by examiner

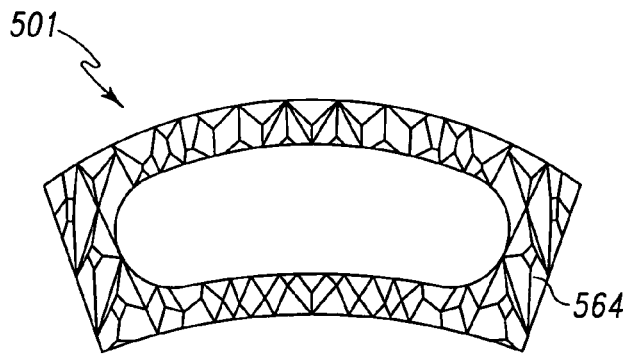
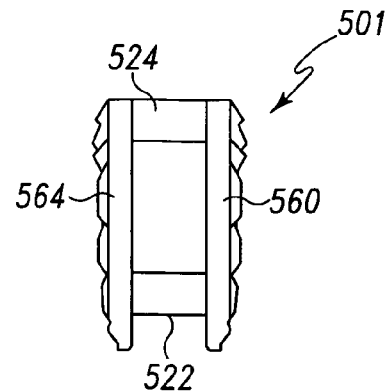
Fig. 21A  Fig. 21B
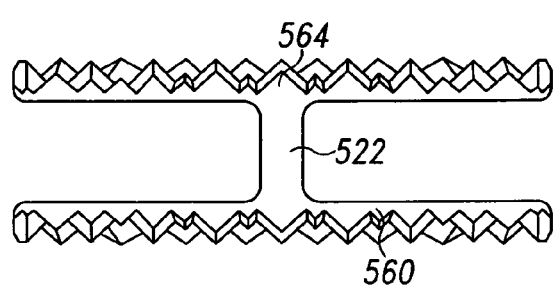
Fig. 21C
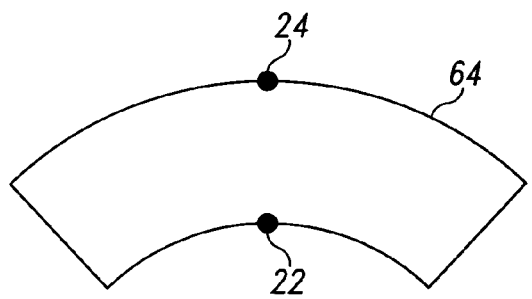
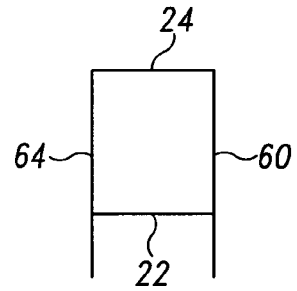
Fig. 22A  Fig. 22B
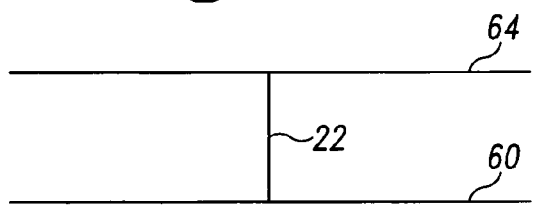
Fig. 22C

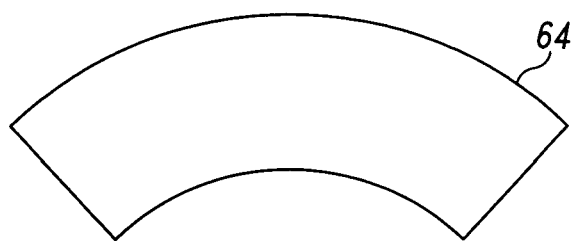
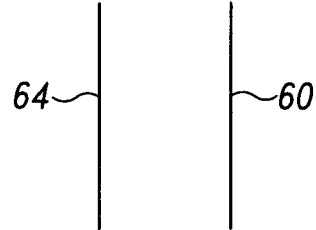
Fig. 25A                Fig. 25B
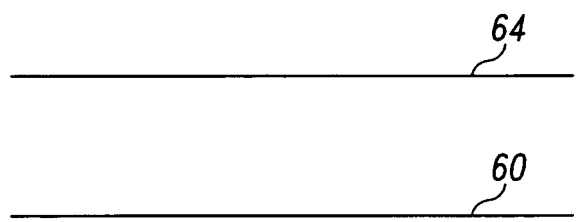
Fig. 25C
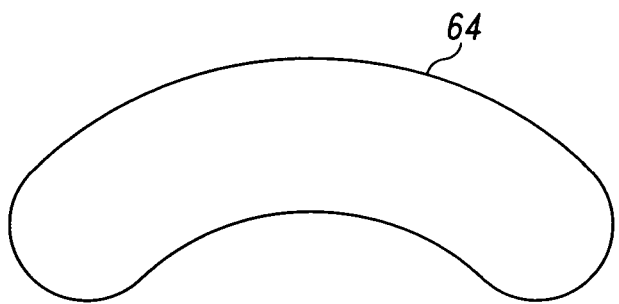
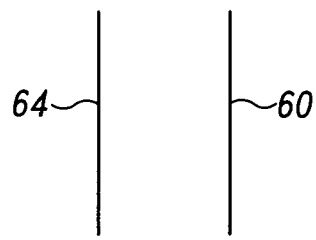
Fig. 26A                Fig. 26B
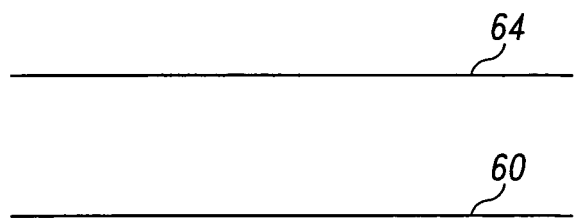
Fig. 26C

TRANSFORAMINAL HYBRID IMPLANT

CROSS REFERENCE

This application claims priority from U.S. Provisional Patent Application Ser. No. 60/720,555, filed on Sep. 26, 2005, entitled "Hybrid Intervertebral Spinal Fusion Implant." The following applications also claim priority to the above referenced provisional application and are related to the present application. They are incorporated by reference herein:

U.S. Utility patent application Ser. No. 11/527,123 filed on Sep. 26, 2006 and entitled "Anterior Hybrid Implant;" and U.S. Utility patent application Ser. No. 11/527,122 filed on Sep. 26, 2006 and entitled "Hybrid Intervertebral Spinal Fusion Implant."

TECHNICAL FIELD

The present invention relates generally to the field of medical implants and methods, and more specifically to interbody spinal implants which may be adapted for placement into an implantation space created across the height of a disc space between two adjacent vertebral bodies for the purpose of correcting disease, dysfunction, or degeneration at that interspace, and any related methods. The spinal implants may be made of a plurality of implant materials, which bear differing degrees of radiographic lucency. These materials may include bone and may or may not be resorbable. The implants of some embodiments are adapted such that radiographic visualization of operative placement and eventual bone healing can be observed.

BACKGROUND

Implants for placement in the intervertebral space between adjacent vertebral bodies in the spine come in a wide range of shapes and sizes. These implants are usually made entirely of one material, although the type of material can vary significantly between specific implants. Such implants for use in human spinal surgery include implants made entirely of metals, such as titanium or stainless steel, or synthetic radiolucent materials such as carbon-carbon composites or poly-ether-ether-ketone (PEEK). Implants may have a structure designed to promote fusion across adjacent vertebral bodies by allowing bone to grow through and around the implant. The operative placement of intervertebral implants is optimized by radiographic opacity. However, a relatively radiolucent implant material optimizes postoperative evaluation of bone growth and fusion across an intervertebral space. While these implants may contain marking beads or radio opaque markers they do not structurally benefit from radio opaque materials. In some configurations, metals, some of which are opaque on radiographs, provide greater strength and resistance to impaction during implantation. Metallic implants may offer reduced wall thickness of structural components and offer increased volume for bone graft and other agents within an implant.

As it is desirable to take advantage of benefits of radiolucent and radio-opaque materials in an implant, there exists a need for an improved implant made of different structural materials with different properties of radiographic appearance. For some implants, it is desirable to provide optimization of mechanical properties, while permitting generous bone filling and bone through-growth. These characteristics may be applied in some embodiments in combination with an ability to radiographically determine bone-implant interaction and bone growth into and around the implant.

SUMMARY

Embodiments of the invention may include an artificial interbody spinal fusion implant made of structural materials with varying radiolucency and mechanical characteristics. Implants may be provided for insertion at least in part into an implantation space formed across the height of a disc space between adjacent vertebral bodies of a human spine. The implant of some embodiments consists of at least two radiographically distinct imaging materials: a radiolucent portion, and a radio-opaque portion. The radio-opaque materials of some embodiments are arranged toward the vertebral endplates with minimal obstruction to radiographic visualization through the implant from anterior to posterior and/or from lateral directions. Embodiments of the implant may include upper and lower portions adapted to be placed within the intervertebral space to contact and support the adjacent vertebral bodies. Upper and lower portions of the implant may include at least one opening in communication with one another and adapted to hold bone growth promoting material and/or bone graft for permitting the growth of bone from vertebral body to vertebral body through the implant. Embodiments of the invention include an artificial interbody spinal implant containing at least two different materials for insertion at least in part into an implantation space formed across the height of a disc space between adjacent vertebral bodies of a spine. Implant embodiments may employ materials that bear a structural role in the design of the implant, and at least a portion of a leading end of the implant may have a reduced height to facilitate insertion of said implant between the two adjacent vertebral bodies. Implants may have a maximum length less than and approximating the posterior to anterior or right to left length of the vertebral bodies. Some embodiments also include a bone engaging surface formed on the exterior of at least the upper and lower portions for engaging the adjacent vertebral bodies, such as one or more protrusions, ratchets, spikes, roughened surfaces or knurling. Embodiments of the implant may be combined with a bone growth or bone healing promoting material such as, but not limited to, bone, bone derived products, demineralized bone matrix, mineralizing proteins, ossifying proteins, bone forming cell differentiating substance, bone morphogenetic protein, hydroxyapatite, and gene therapy material leading to the production of bone. Embodiments of the implant may also be combined with a therapeutic substance for the treatment of infection, tumor or other pathologic process. In some embodiments of the invention, one component material is relatively, or absolutely radiolucent. In some embodiments of the invention, one component material is radio-opaque. One component material of the implant may be at least in part resorbable. In some embodiments, at least a portion of an implant is treated to promote bone in-growth between the implant and adjacent vertebral bodies. Embodiments of the implant may be used in combination with at least one spinal fixation implant. Embodiments of the implant may include a hollow interior and at least one area for attachment or interaction with an insertion device for surgical placement or removal from the intervertebral space. Upper and lower surfaces of some embodiments of the implant may include a plurality of openings. Embodiments of the implant may be designed to be inserted adjacent to a second implant into a disc space between adjacent vertebral bodies, the second implant being of identical or differing shape. At least one opening may be between the leading and trailing ends of embodiments of the implant. Upper and lower portions or surfaces of embodiments of the implant may be at least in part generally parallel to one another or may be configured with an angular relationship to each other for allowing angulation of adjacent vertebral bodies relative to each other.

Another embodiment of the invention is an intervertebral implant configured for implantation from a transforaminal surgical approach. The implant may include a generally convex anterior sidewall, a generally concave posterior sidewall, a proximal end between the anterior and posterior sidewalls, and a distal end between the anterior and posterior sidewalls and generally opposite from the proximal end. Embodiments include a superior portion coupled to the anterior and posterior sidewalls for engaging a superior vertebral body, and an inferior portion coupled to the anterior and posterior sidewalls for engaging an inferior vertebral body. The implant may have a first material with a detectable radiographic signature and a second material with a radiographic signature less detectable than the radiographic signature of the first material.

Yet another embodiment of the invention is an intervertebral implant with a lateral dimension, an anterior to posterior dimension, and an inferior to superior vertical dimension, the implant being configured for implantation from a transforaminal surgical approach. Embodiments of the implant include a first body made at least in part from a radiographically detectable material and including two or more supports providing structural support in the vertical dimension, the first body including an at least partially generally convexly curved anterior sidewall and an at least partially generally concavely curved posterior sidewall, and a second body coupled to the first body and made at least in part from a material that is less radiographically detectable than the material of the first body. A relative alignment among two or more of the supports, as viewed radiographically from at least one of the anterior, posterior, and lateral sides, may indicate a rotational position of the implant about a vertical axis.

Still another embodiment of the invention is an intervertebral implant configured for implantation from a transforaminal surgical approach that may include a generally convex anterior sidewall, a generally concave posterior sidewall, and a superior portion coupled to the anterior and posterior sidewalls for engaging a superior vertebral body. The implant embodiment may also include an inferior portion coupled to the anterior and posterior sidewalls for engaging an inferior vertebral body, a proximal end between the anterior and posterior sidewalls made at least in part of a radiolucent material, and a distal end between the anterior and posterior sidewalls and generally opposite from the proximal end made at least in part of a radiolucent material.

An embodiment of the invention is an intervertebral implant configured for implantation from a transforaminal surgical approach that has a body with a generally convex anterior sidewall, a generally concave posterior sidewall, a superior portion coupled to the anterior and posterior sidewalls for engaging a superior vertebral body, and an inferior portion coupled to the anterior and posterior sidewalls for engaging an inferior vertebral body. The implant may include a proximal end between the anterior and posterior sidewalls made at least in part of material with a lower modulus of elasticity than the body, and a distal end between the anterior and posterior sidewalls and generally opposite from the proximal end made at least in part of material with a lower modulus of elasticity than the body.

Embodiments of the invention may include a method of implanting an intervertebral implant from a transforaminal surgical approach. The method includes providing an implant comprising: a generally convex anterior sidewall, a generally concave posterior sidewall, a superior portion for engaging a superior vertebral body, an inferior portion for engaging an inferior vertebral body, a proximal end between the anterior and posterior sidewalls made at least in part of a radiolucent material, and a distal end between the anterior and posterior sidewalls and generally opposite from the proximal end made at least in part of a radiolucent material. The method may also include radiographically observing placement of the implant between the superior and inferior vertebral bodies through one or more of the proximal and distal ends, the anterior sidewall, and the posterior sidewall, and radiographically observing bone growth between the superior and inferior vertebral bodies through one or more of the proximal and distal ends, the anterior sidewall, and the posterior sidewall.

Another embodiment of the invention is a method of assembling a transforaminal intervertebral implant. The method includes providing a body comprising: a generally convex anterior sidewall, a generally concave posterior sidewall, a superior portion for engaging a superior vertebral body, and an inferior portion for engaging an inferior vertebral body. The method may also include applying a distal end between the anterior and posterior sidewalls, the distal end having less of a radiographic signature than the body.

BRIEF DESCRIPTION OF THE DRAWINGS

FIGS. 21A, 21B, and 21C are plan (axial), side (lateral), and posterior views respectively of components of an embodiment of the invention.

FIGS. 22A, 22B, and 22C are graphical representations of at least the implant of FIGS. 21A, 21B, and 21C in plan (axial), side (lateral), and posterior views respectively.

FIGS. 25A, 25B, and 25C are graphical representations of embodiments of an implant of the invention in plan (axial), side (lateral), and posterior views respectively.

FIGS. 26A, 26B, and 26C are graphical representations of embodiments of an implant of the invention in plan (axial), side (lateral), and posterior views respectively.

DETAILED DESCRIPTION

The following description is intended to be representative only and not limiting and many variations can be anticipated according to these teachings, which are included within the scope of this inventive teaching. Reference will now be made in detail to embodiments of this invention, examples of which are illustrated in the accompanying drawings. Wherever possible, the same reference numbers will be used throughout the drawings to refer to the same or like parts.

Figure 1:
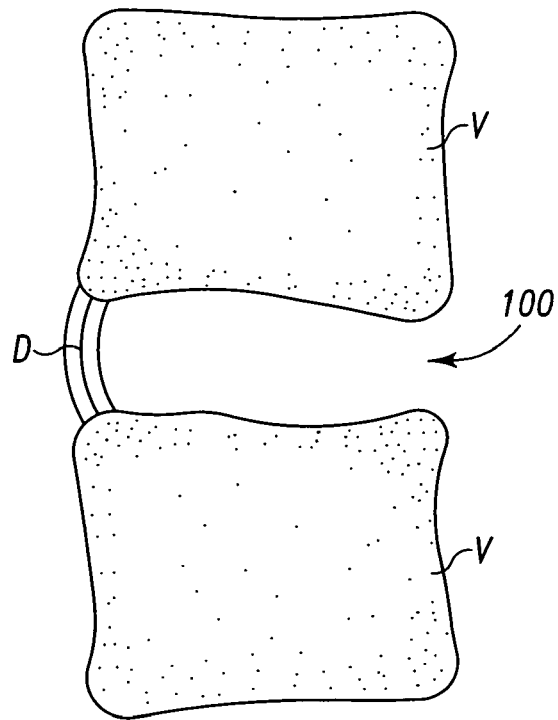
FIG. 1 is a side view of two adjacent vertebral bodies in a lumbar spine with an implantation space formed across the height of the spinal disc space.
Figure 2:
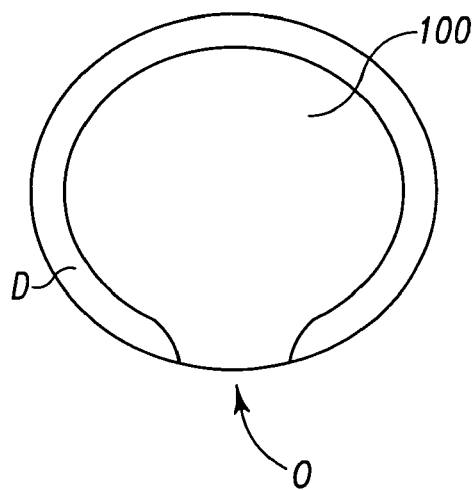
FIG. 2 is a top plan view of a vertebral body in a lumbar spine with an implantation space formed through a posterior approach.
Figure 3:
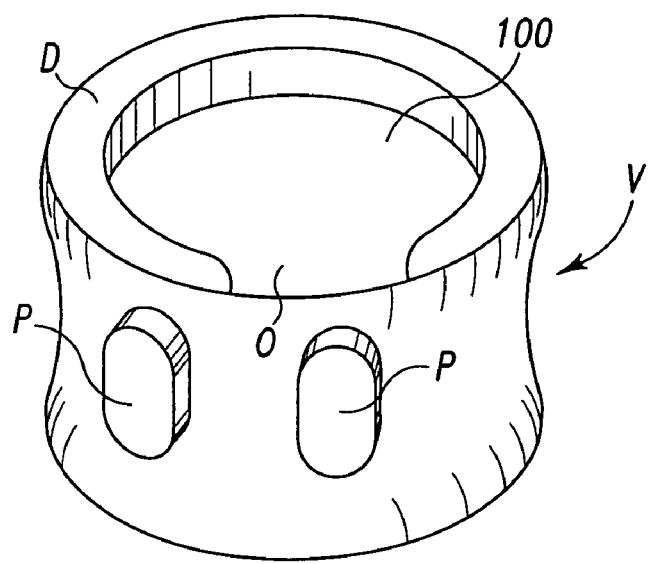
FIG. 3 is a side perspective view of the implantation space of FIG. 2.

FIGS. 1-3 show an implantation space 100 formed across the height of a spinal disc D between vertebral bodies V in the lumbar spine. In other embodiments, the vertebral bodies may be bodies of the cervical or thoracic spine as well. It is understood that numerous methods exist and that any method and instrumentation designed for the purpose may be applied to prepare the desired implantation space and perform disc and soft tissue removal in such a manner as to be adapted to receive the implants of the present invention. It is also understood that implantation space preparation commonly leaves residual disc material D prior to implant placement.

FIG. 3 shows the implantation space 100, which has been prepared by partial disc and soft tissue removal adjacent to the vertebral body V. The preparation in FIG. 3 is shown as a posterior lumbar surgical approach, and the opening O into the disc space from the posterior is shown. The opening O may also be an opening prepared for transforaminal or oblique surgical approaches. Residual portions P of the vertebral pedicles are also shown.

Figure 4:
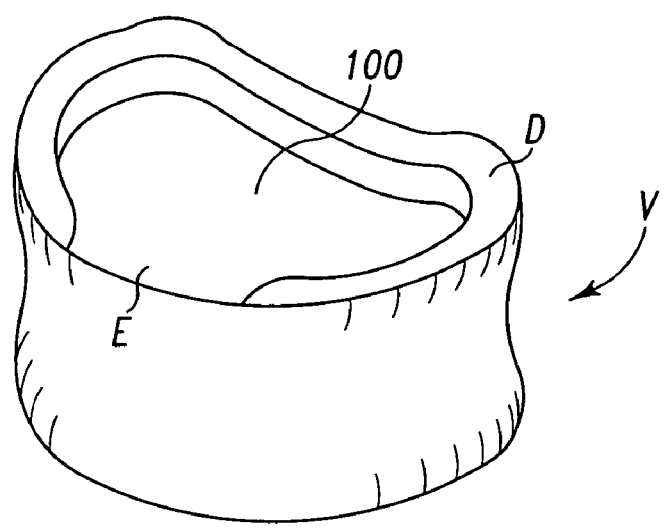
FIG. 4 is a perspective view of an implantation space formed through an anterior approach.

FIG. 4 shows the implantation space 100, which has been prepared by partial disc and soft tissue removal adjacent to the vertebral body V. The preparation in FIG. 4 is shown as an anterior surgical approach and the entrance E into the disc space from the anterior is shown. This representation can reflect a cervical, thoracic, or lumbar spinal intervertebral space preparation.

Figure 5:
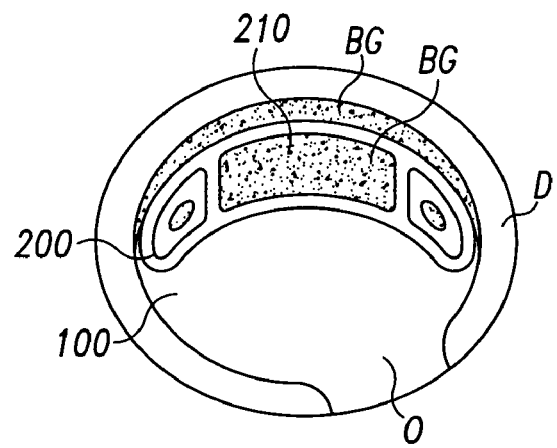
FIG. 5 is a top plan view of a vertebral body in the lumbar spine with an embodiment of an implant positioned in the implantation space of FIG. 2.

FIG. 5 shows a unilateral implant 200 seated in the implantation space 100 in accordance with an embodiment of the present invention. Bone graft material BG is shown anterior to the unilateral implant 200, as well as within a central void 210 of the unilateral implant 200.

Figure 6:
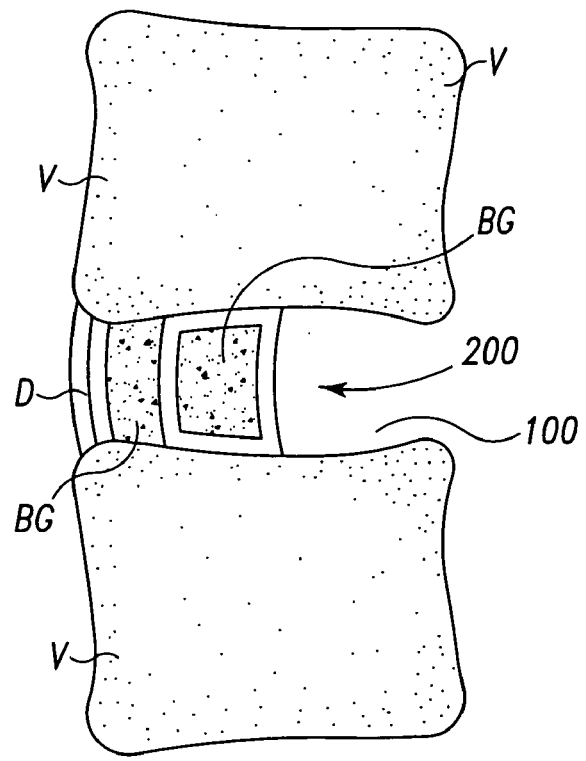
FIG. 6 is a side view of two adjacent vertebral bodies with the implant of FIG. 5 positioned in the implantation space of FIG. 2 through a posterior approach.

FIG. 6 shows a unilateral implant 200 seated in the implantation space 100. Bone graft material BG is shown anterior to the unilateral implant 200 but posterior to remaining disc D, as well as within the central void 210 of the unilateral implant 200.

Figure 7:
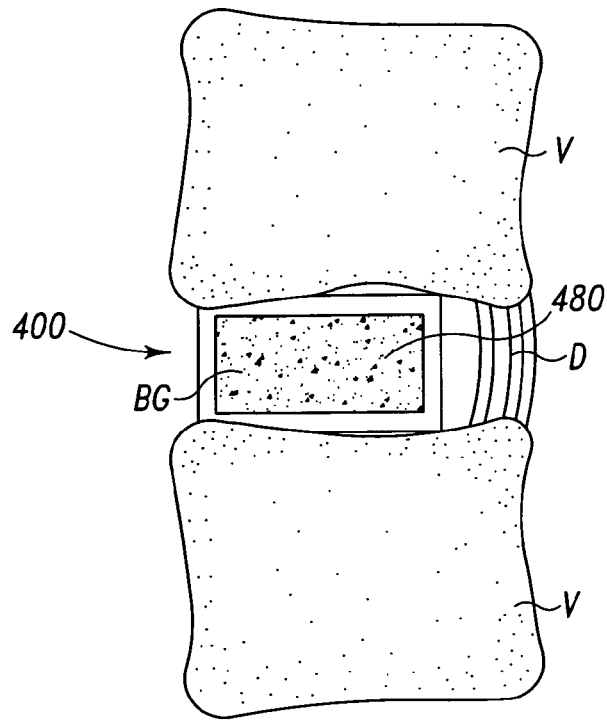
FIG. 7 is a side view of two adjacent vertebral bodies with an implant positioned in the implantation space of FIG. 2 through an anterior approach.

FIG. 7 shows an anterior implant 400 seated in the implantation space 100. Bone graft material BG is shown within a cavity 480 of the anterior implant 400.

Figure 8:
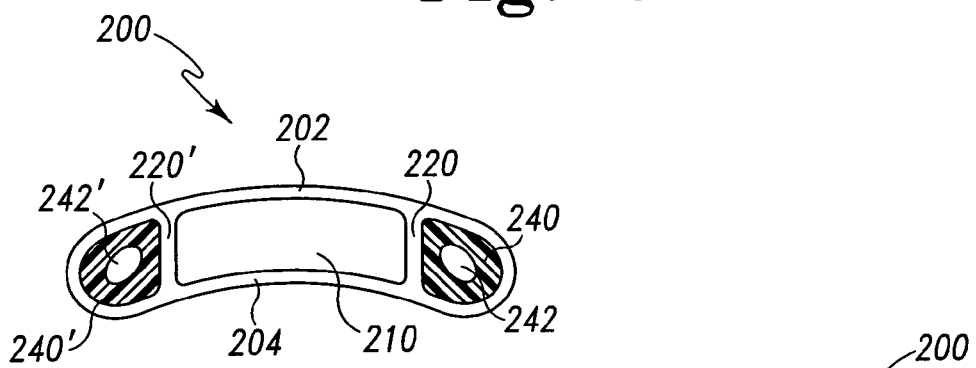
FIG. 8 is a top plan view of the implant of FIG. 5

FIG. 8 shows the unilateral implant 200 with an anterior aspect 202 and a posterior aspect 204. The central void 210 is shown. Traversing support structures 220, 220' extend from anterior 202 to posterior 204 aspects of the implant. In the lateral aspects of the unilateral implant 200 radiolucent blocks 240, 240' are shown, each with a central cavity 242, 242'.

Figure 9:
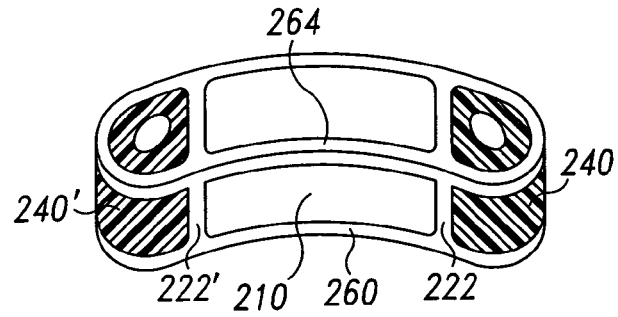
FIG. 9 is a rear perspective view of the implant of FIG. 5.

FIG. 9 shows the unilateral implant 200 as described in FIG. 8. The view from a posterior perspective shows the central void 210, the radiolucent blocks 240, 240' and posterior support columns 222, 222' which extend from an inferior aspect 260 to a superior aspect 264 of the implant.

Figure 10:
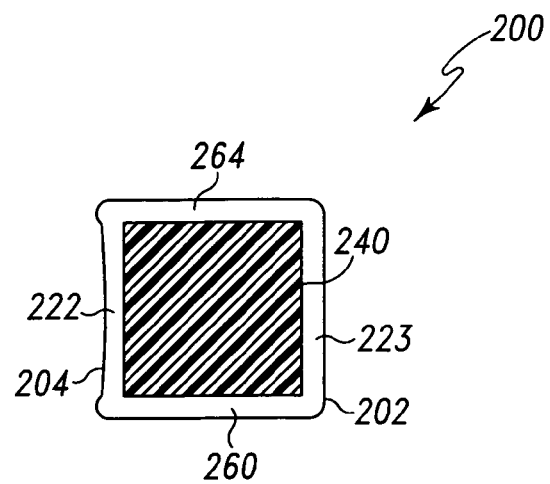
FIG. 10 is a side view of the implant of FIG. 5.

FIG. 10 shows the unilateral implant 200 as described in FIG. 8 from a lateral view. The radiolucent block 240 is shown positioned between the superior aspect 264 and the inferior aspect 260 of the implant. A posterior support column 222 and an anterior support column 223 between the superior aspect 264 and inferior aspect 260 are shown. In a lateral projection, anterior 202 and posterior 204 aspects to the implant are noted.

Figure 11:
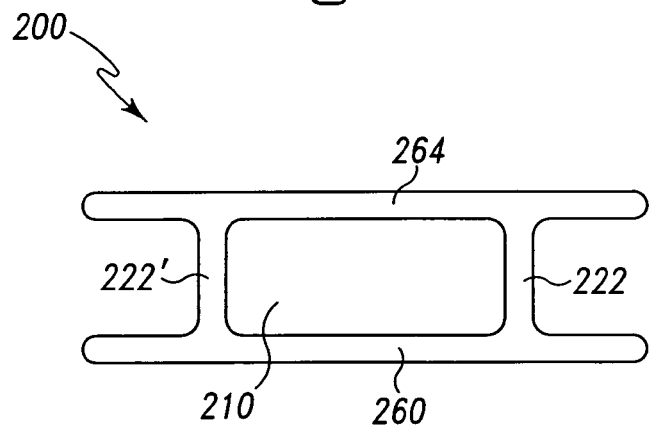
FIG. 11 is a rear view of the implant of FIG. 5.

FIG. 11 shows a posterior view of the implant as described in FIGS. 8 and 9 without appearance of the radiolucent blocks 240, 240', in order to show radiographic appearance. Only the posterior support columns 222, 222' extending between the inferior aspect 260 and the superior aspect 264 of the implant are visualized radiographically due to the selected radio-opaque nature of the material implemented in this embodiment. Anterior support columns 223, 223' are hidden behind posterior support columns 222, 222' when the unilateral implant 200 is visualized radiographically directly from the posterior.

Figure 12:
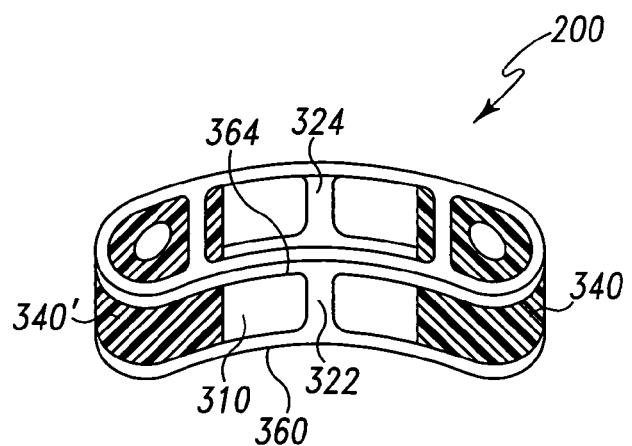
FIG. 12 is a rear perspective view of another embodiment of an implant for use in the implantation space of FIG. 2.

FIG. 12 shows another embodiment of the invention with a center-support implant 300 in rear perspective view. A central volume 310, and radiolucent lateral blocks 340, 340', as well as anterior support structure 324, and posterior support structure 322 are noted.

Figure 13:
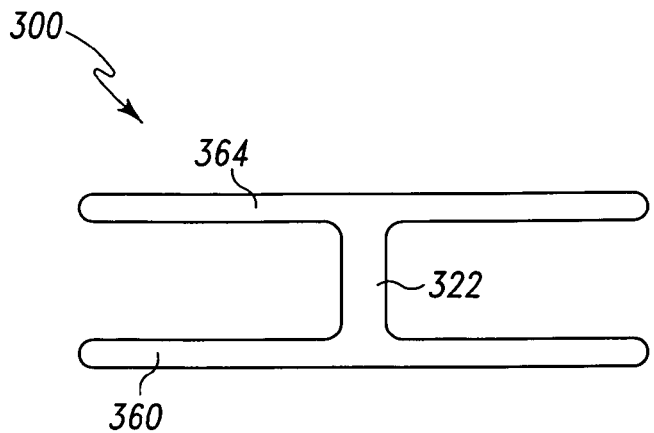
FIG. 13 is a rear view of the implant of FIG. 12.

FIG. 13 shows a posterior view of the implant as described in FIG. 12 without appearance of the radiolucent lateral blocks 340, 340' in order to show radiographic appearance. Only the posterior support structure 322, which overlaps in this view the anterior support structure 324, seen in FIG. 12, is visualized radiographically between the inferior portion 360 and the superior portion 364 of the implant due to the selected radio-opaque nature of the material implemented in this embodiment.

Figure 14:
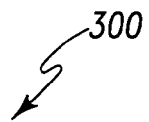
FIG. 14 is a side view of the implant of FIG. 12.
Figure 14:
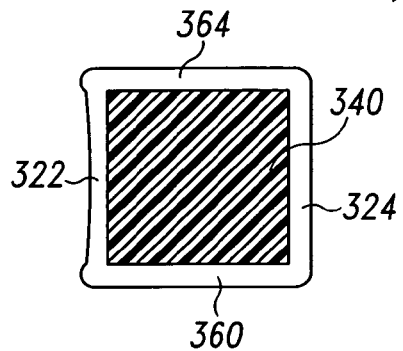

FIG. 14 shows the center-support implant 300 as described in FIG. 12 from a lateral view. The radiolucent lateral block 340 is shown positioned between the superior portion 364 and the inferior portion 360 of the implant. In this lateral projection the anterior support structure 324 and posterior support structure 322 of the implant are noted.

Figure 15:
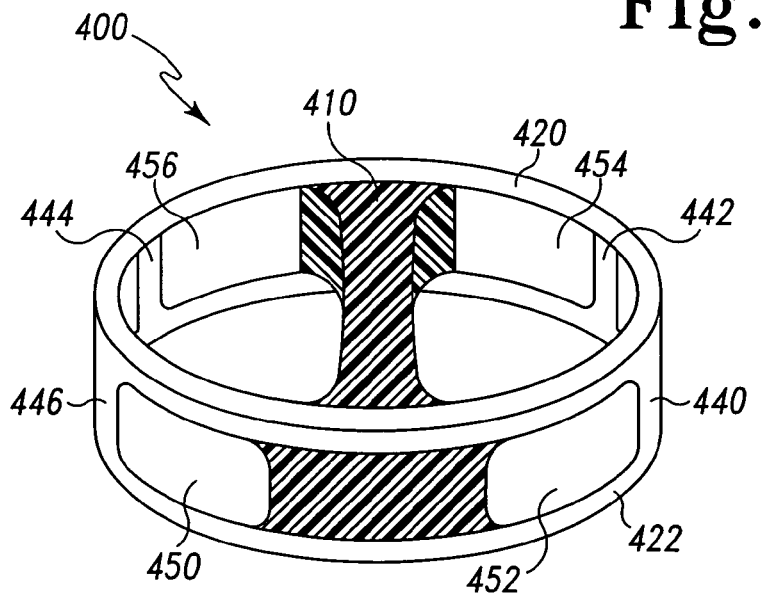
FIG. 15 is a rear perspective view of an embodiment of an implant suited for anterior placement into a cervical or lumbar intervertebral disc space.

FIG. 15 illustrates an anterior implant 400. In some embodiments, the anterior implant 400 may be placed through an anterior surgical approach. However, the anterior implant 400 may also be placed by other surgical approaches such as, but not limited to, an anterior-oblique approach or a lateral approach. A large central strut 410 made of radiolucent material is shown traversing the implant. Upper rim 420 and lower rim 422 are attached to the central strut 410 and further supported and connected to one another through supportive structures 440, 442, 444, 446. Openings through the sides of the implant are noted 450, 452, 454, 456. These openings may permit for the growth of bone through and into anterior implant 400, though the invention is not so limited.

Figure 16:
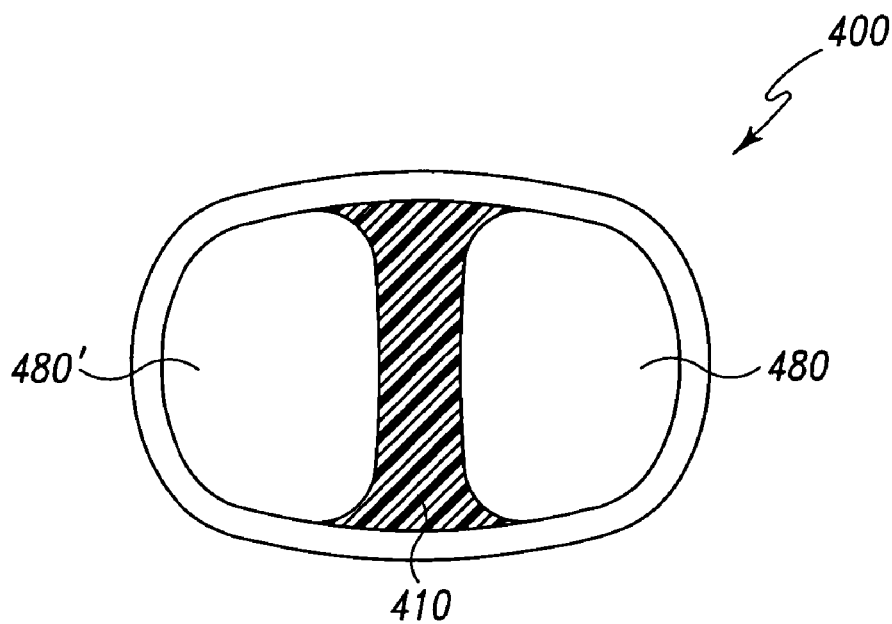
FIG. 16 is a top plan view of the implant of FIG. 15.

FIG. 16 shows a top plan view of the anterior implant 400 as described in FIG. 15. The large central strut 410 is noted. Two cavities 480,480' within the anterior implant 400 are shown on either side of the strut 410. These cavities may permit for the growth of bone through and into anterior implant 400, though the invention is not so limited.

Figure 17:
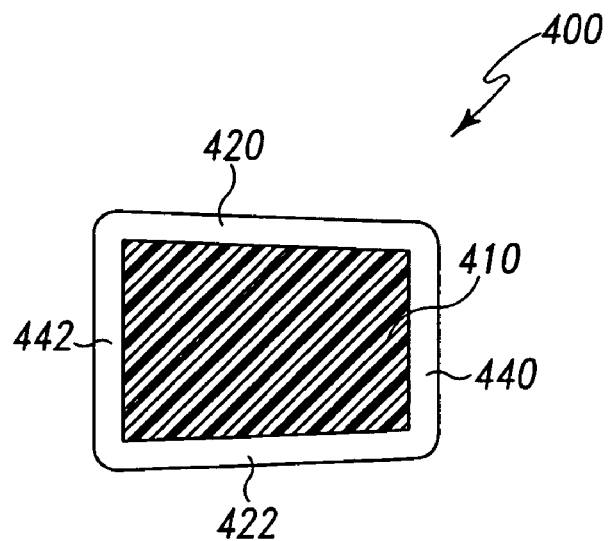
FIG. 17 is a side view of the implant of FIG. 15.

FIG. 17 shows a lateral view of the anterior implant 400 as described in FIGS. 15 and 16. Upper rim 420 and lower rim 422 are shown, as is the lateral view of the central strut 410. Given the radiolucent nature of the central strut 410, on radiographic visualization only the upper rim 420 and lower rim 422 as well as radio-opaque supportive structures 440,442 would be noted. The remaining two supportive structures 444,446 noted in FIG. 15 are obscured in a lateral view by the supportive structures 440,442. Further, angulation between the upper rim 420 and lower rim 422 may facilitate insertion of anterior implant 400 between the two adjacent vertebral bodies and permit control of sagittal plane intervertebral alignment.

Figure 18:
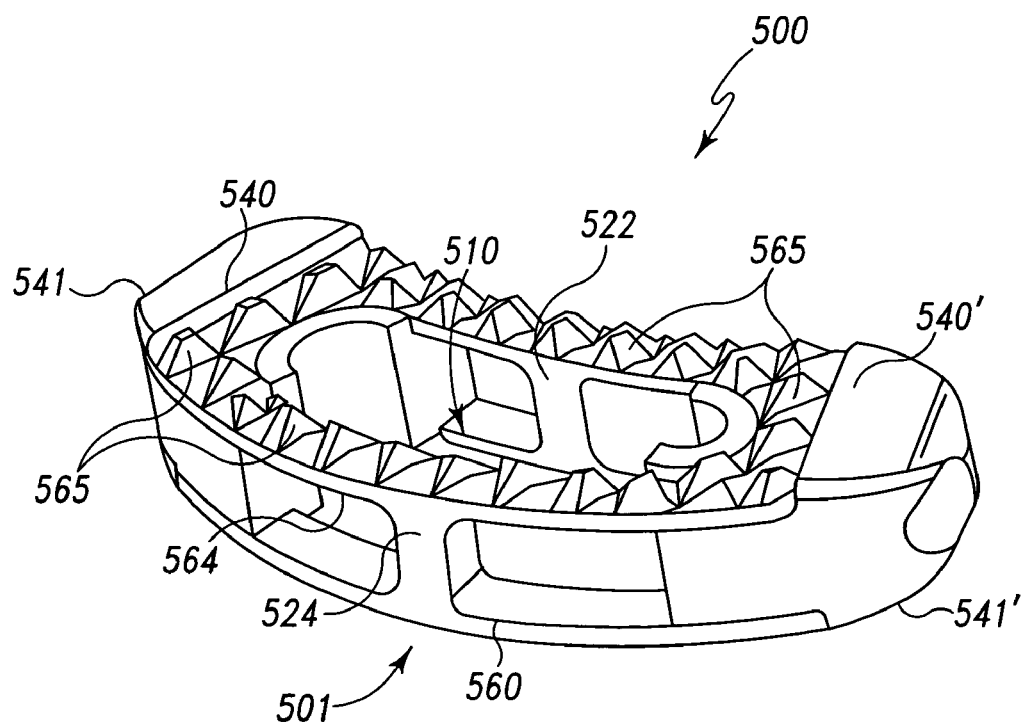
FIG. 18 is a perspective view of an implant embodiment of the invention.
Figure 19:
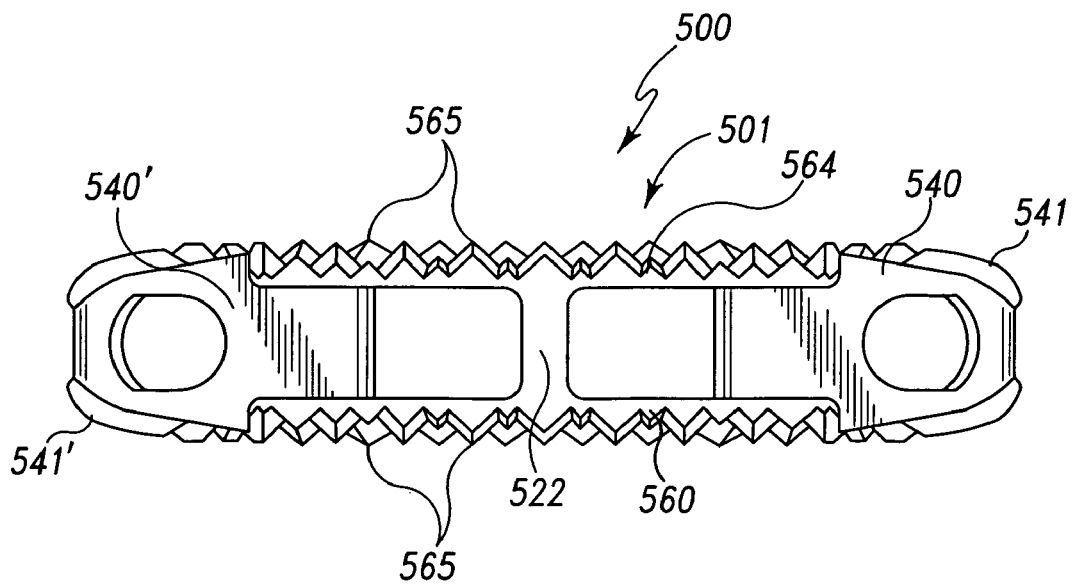
FIG. 19 is a rear view of the implant of FIG. 18.
Figure 20:
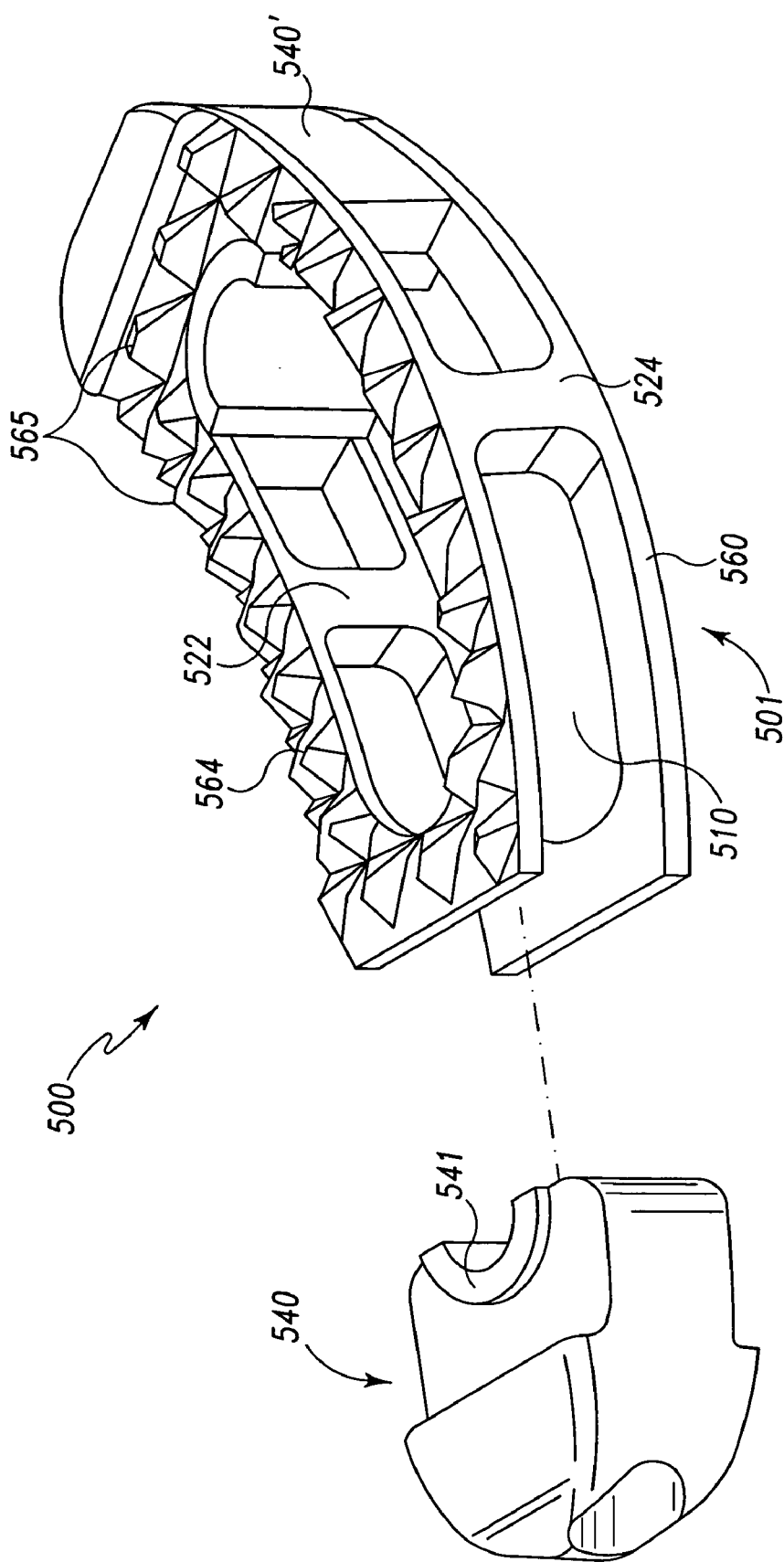
FIG. 20 is a partially exploded perspective view of the implant of FIG. 18.

FIGS. 18-20 illustrate another implant embodiment of the invention. A laterally extended implant 500 is shown in perspective view in FIG. 18. A rear view is shown in FIG. 19, and a partially exploded perspective view is illustrated in FIG. 20. The laterally extended implant 500 is similar to the center-support implant 300, at least with respect to its pattern of support members, but includes lateral blocks 540, 540' that extend beyond the lateral extents of a central body 501. The central body 501 is constructed at least in part of material with a different radiographic signature than the lateral blocks 540, 540'. The central body 501 includes a posterior support member 522 and an anterior support member 524. The support members 522, 524 couple between an inferior plate 560 and a superior plate 564. A number of teeth or protrusions 565 are illustrated on both the inferior plate 560 and the superior plate 564. The protrusions 565 may assist the implant in engaging bone surfaces. In embodiments where the central body 501 is made from a metallic material, an advantage may be established in forming protrusions 565. Metal teeth, protrusions, and other surface characteristics may be both stronger and capable of being more effectively sharpened to better engage bone surfaces.

The laterally extended implant 500 is a hybrid adaptation of the CRESCENT™ implant marketed by Medtronic, Inc. Several unique features of the CRESCENT™ implant, associated instruments, and methods, and similarly constructed implants, are detailed in U.S. patent application Ser. No. 11/107,192, entitled, "Instruments, Implants and Methods for Positioning Implants into a Spinal Disc Space," filed Apr. 15, 2005, which is hereby incorporated by reference in its entirety herein. Recess areas and receptacles in the lateral blocks 540, 540' near the lateral extents of the laterally extended implant 500, useful at least for instrument engagement, are more fully described in the '192 application.

Each of the lateral blocks 540, 540' illustrated in FIG. 19 includes a reduced height section 541, 541' to facilitate insertion of the laterally extended implant 500. In some embodiments, the laterally extended implant 500 may be inserted with either of the lateral blocks 540, 540' as the insertion end. An implant configured for insertion from either direction reduces inventory requirements and enhances flexibility during surgical procedures. Reduced height sections such as these may be applied to unilateral implant 200, center-support implant 300, and other implants not specifically detailed herein.

The laterally extended implant 500 also includes a central cleft 510 suitable for receiving bone grafting material. Openings through the anterior and posterior of the laterally extended implant 500, as well as through the inferior plate 560 and the superior plate 564 are provided in some embodiments of the invention. These openings may be useful to permit bone growth to occur into, out of, and through the laterally extended implant 500.

The lateral block 540 illustrated in FIG. 20 includes a ridge 541 that provides interference between the lateral block 540 and the central body 501. The ridge 541 may be formed in the lateral block 540 separately by a manufacturing process such as milling, casting, or injection molding, or the ridge 541 may be a result of the material of the lateral block 540 being cast, formed, injected, or molded directly around the central body 501. In some embodiments, a separately formed lateral block 540 is snapped into place on a central body 501.

As illustrated in FIG. 18, the lateral blocks 540, 540' are shown approximately even with anterior and posterior extents of the central body 501. However, in some embodiments, the lateral blocks 540, 540' may extend beyond the anterior and posterior extents of the central body 501 or encapsulate at least portions of the central body 501.

In some embodiments, implants of multiple sizes and configurations may be formed by assembling various, cooperating central bodies 501 and lateral blocks 540, 540' of varying sizes. An embodiment of the invention may include a kit of variously sized central bodies 501 and variously sized lateral blocks 540, 540' that are intended to be assembled by surgeons, product resellers, and other distributors.

Embodiments of implants configured for implantation from a transforaminal approach have been specifically described in association with unilateral implant 200, center-support implant 300, and laterally extended implant 500. These and other embodiments of the invention may be described as having a generally convex anterior sidewall, and a generally concave posterior sidewall. A generally convex sidewall may have a smooth convex curve, or may be a portion of segments, including indentations, that generally represent a convex shape. A generally concave sidewall may have a smooth concave curve, or may be a portion of segments, including indentations, that generally represent a concave shape. The term sidewall may be a solid wall, may include a wall with a number of openings, or may be merely the respective anterior or posterior extents of an implant. The anterior extent of embodiments of the invention may include, for example, edges of the inferior aspect 260, the inferior portion 360, the inferior plate 560, the superior aspect 264, the superior portion 364, and the superior plate 564. The anterior extent may also include anterior edges of blocks such as radiolucent blocks 240, 240', radiolucent lateral blocks 340, 340', and lateral blocks 540, 540', and may include supports along anterior portions such as anterior support column 223, 223', anterior support structure 324, and anterior support member 524.

The posterior extent of embodiments of the invention may include, for example, edges of the inferior aspect 260, the inferior portion 360, the inferior plate 560, the superior aspect 264, the superior portion 364, and the superior plate 564. The posterior extent may also include posterior edges of blocks such as radiolucent blocks 240, 240', radiolucent lateral blocks 340, 340', and lateral blocks 540, 540', and may include supports along posterior portions such as posterior support column 222, 222', posterior support structure 322, and posterior support member 522.

Embodiments of implants configured for implantation from a transforaminal approach may be additionally defined as having proximal and distal ends between the anterior and posterior sidewalls, the proximal and distal ends being generally opposite from one another. In some embodiments, the end of the implant that is proximal or distal may be defined by the direction from which the implant is inserted, the distal end being the end of the implant inserted first.

Examples of inferior portions of implants coupled to anterior and posterior sidewalls include the inferior aspect 260, the inferior portion 360, and the inferior plate 560. Examples of superior portions of implants coupled to anterior and posterior sidewalls include the superior aspect 264, the superior portion 364, and the superior plate 564. The inferior and superior portions may be configured to engage inferior and superior vertebral bodies respectively.

Embodiments of implants configured for implantation from a transforaminal approach may also include a first material with a detectable radiographic signature and a second material with a radiographic signature less detectable than the radiographic signature of the first material. For example, the unilateral implant 200 includes posterior support columns 222, 222', and anterior support columns 223, 223', and at least portions of the inferior aspect 260 and the superior aspect 264 that are made from a first material that has a detectable radiographic signature. Radiolucent blocks 240, 240' are a less radiographically detectable second material. The term radiographic signature as used herein refers to a resulting visualization on radiographic devices. A radiolucent block, for example, is faintly to indistinguishably visible on a radiograph, and would therefore be considered to have less of a radiographic signature than a radio-opaque metal such as titanium.

Embodiments of the center-support implant 300 also include a first material with a detectable radiographic signature and a second material with a radiographic signature less detectable than the radiographic signature of the first material. Posterior support structure 322 and anterior support structure 324, and at least portions of the inferior portion 360 and the superior portion 364 include a first material with a detectable radiographic signature. The radiolucent lateral blocks 340, 340' are a second material with a radiographic signature less detectable than the radio graphic signature of the first material. The laterally extended implant 500 is another example and includes a central body 501 at least in part made from a first material with a detectable radiographic signature, and lateral blocks 540, 540' that include a second material with a radiographic signature less detectable than the radiographic signature of the first material.

Second materials such as radiolucent blocks 240, 240', radiolucent lateral blocks 340, 340', and lateral blocks 540, 540' may also be made at least in part of material with a lower modulus of elasticity than the central body 501. In some circumstances, it may be desirable to provide a modulus of elasticity that more nearly approximates the modulus of elasticity of bone, or that at least reduces that rigidity of the implant somewhat.

FIGS. 21A, 21B, and 21C are plan, side, and posterior views respectively of the central body 501. The lateral blocks 540, 540' have been removed from these figures, which is consistent with radiographic views which would be presented where the lateral blocks are made from less radiographically visible or radiolucent material. FIG. 21A is a plan view consistent with an axial radiographic image. FIG. 21B is a side view consistent with a lateral radiographic image. FIG. 21C is a posterior view consistent with a posterior to anterior radiographic image.

FIG. 21B illustrates a side or lateral view of the central body 501. The outermost portions of the inferior plate 560 and the superior plate 564 are shown in a non-parallel angular relationship. Particularly, the central body 501 is taller near the anterior portion of the implant. As configured, the laterally extended implant 500 when placed in a disc space would provide angulation between endplates of the superior and inferior adjacent vertebral bodies. This configuration may be useful in restoring lordotic curvature to a spine. In other embodiments, the height may be greater near a posterior portion of the implant to help restore kyphotic curvature to a spine. Although the length of the posterior support member 522 and the anterior support member 524 are substantially the same in the illustrated embodiment, an angular relationship is created in the central body 501 by varying the thicknesses of the inferior plate 560 and the superior plate 564.

FIGS. 22A-29C are simplified graphical representations of various configurations of transforaminal implants. Each implant will be represented by an inferior portion 60, a superior portion 64, posterior supports 22, 22', anterior supports 24, 24', end supports 25, 25' where appropriate. Each of the supports is represented here as a cylindrical component. However, each may be of any desired configuration, such as but not limited to, rectangular, square, circular, oval, polygonal, or variable in cross-section along its length. Less radiographic or radiolucent blocks, as have been disclosed above, are not shown in these figures, but any size or configuration of such a block is contemplated for each of the implants represented. Although angulation for lordotic and kyphotic correction is not illustrated in FIGS. 22A-29C, such angulation is contemplated for each embodiment. FIGS. 22A-24C and 27A-29C will further illustrate relationships between relative alignments among two or more of the supports, as viewed radiographically from at least one of the anterior, posterior, and lateral sides, and rotational position of the implant about a vertical axis. A vertical axis for the purpose of this orientation is considered vertical as viewed in the posterior views illustrated.

FIGS. 22A-22C represent embodiments of the invention including the more specific embodiment illustrated in FIGS. 21A-21C. Posterior support 22 along the posterior wall of the implant is configured to block radiographic visualization of anterior support 24 when the implant is radiographically viewed from the posterior side of the implant.

Figure 23A:
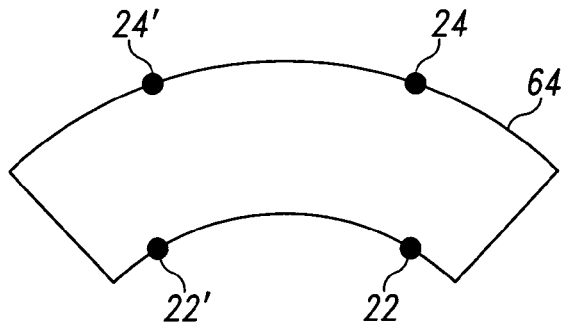
FIGS. 23A, 23B, and 23C are graphical representations of embodiments of an implant of the invention in plan (axial), side (lateral), and posterior views respectively.
Figure 23B:
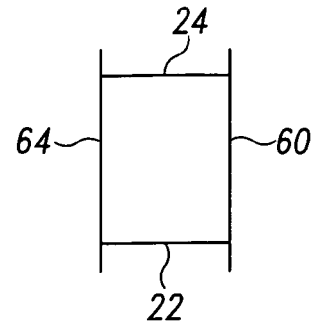
Figure 23C:
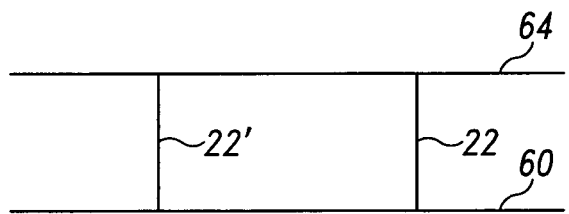

FIGS. 23A-23C show posterior supports 22, 22' along the posterior wall of the implant configured to block radiographic visualization of anterior supports 24, 24' respectively when the implant is radiographically viewed from the posterior side of the implant. The posterior supports 22, 22' placed along the posterior sidewall are each configured to block radiographic visualization of the other, contralateral support when the implant is radiographically viewed from a lateral side of the implant. The anterior supports 24, 24' placed along the anterior sidewall are each configured to block radiographic visualization of the other, contralateral support when the implant is radiographically viewed from a lateral side of the implant.

Figure 24A:
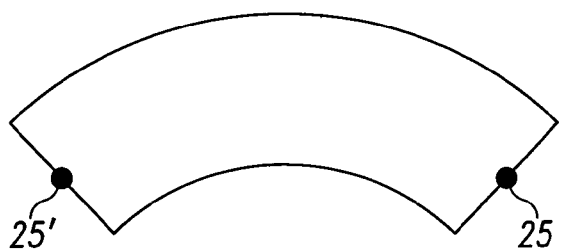
FIGS. 24A, 24B, and 24C are graphical representations of embodiments of an implant of the invention in plan (axial), side (lateral), and posterior views respectively.
Figure 24B:
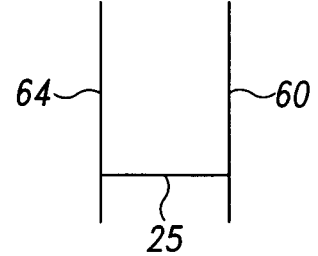
Figure 24C:
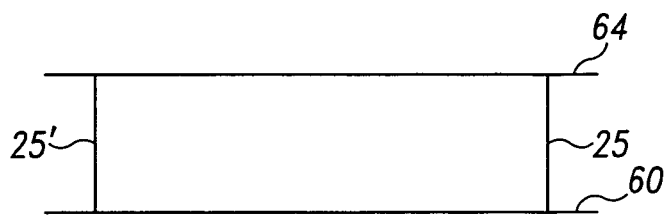

FIGS. 24A-24C show end supports 25, 25' near first and second lateral extents of the implant. Each of the end supports 25, 25' is configured to block radiographic visualization of the other, contralateral support when the implant is radiographically viewed from a lateral side of the implant.

FIGS. 25A-25C illustrate an implant with an inferior portion 60 and a superior portion 64 that are coupled to one another by one or more less radiographically detectable or radiolucent members. The inferior portion 60 and the superior portion 64 are configured to allow lateral extensions to go beyond the lateral extents of the inferior and superior portions 60, 64 in some embodiments.

FIGS. 26A-26C illustrate an implant with an inferior portion 60 and a superior portion 64 that are coupled to one another by one or more less radiographically detectable or radiolucent members. The inferior portion 60 and the superior portion 64 are configured to provide rims around the entire periphery of upper and lower segments of some embodiments of the invention.

Figure 27A:
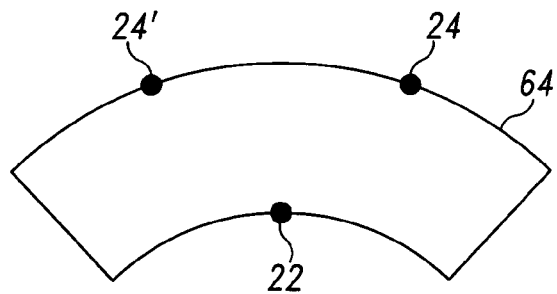
FIGS. 27A, 27B, and 27C are graphical representations of embodiments of an implant of the invention in plan (axial), side (lateral), and posterior views respectively.
Figure 27B:
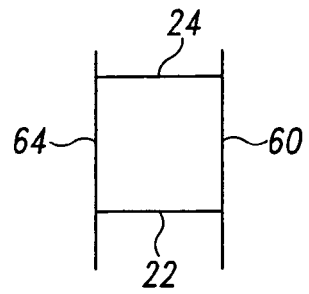
Figure 27C:
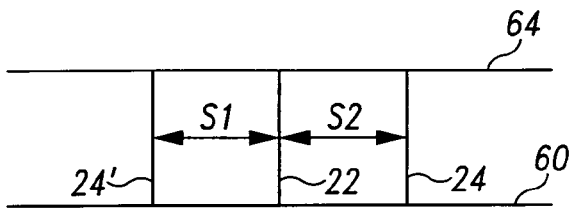

FIGS. 27A-27C show an implant with anterior supports 24, 24' placed along the anterior sidewall that are each configured to block radiographic visualization of the other, contralateral support when the implant is radiographically viewed from a lateral side of the implant. The implant also includes a posterior support 22 placed approximately medially along the posterior sidewall. When the implant is viewed radiographically from a posterior side, lateral space S1 between anterior support 24' and posterior support 22, and lateral space S2 between anterior support 24 and posterior support 22, are substantially equal.

Figure 28A:
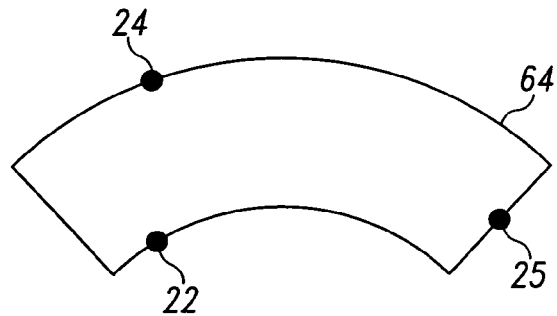
FIGS. 28A, 28B, and 28C are graphical representations of embodiments of an implant of the invention in plan (axial), side (lateral), and posterior views respectively.
Figure 28B:
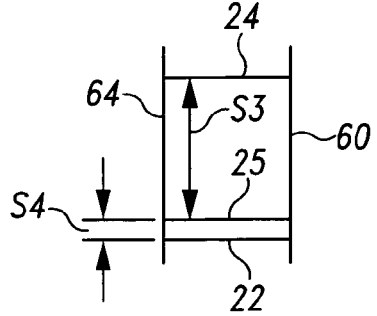
Figure 28C:
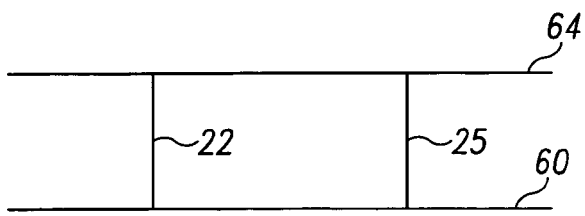

FIGS. 28A-28C show a posterior support 22 along the posterior wall of the implant configured to block radiographic visualization of an anterior support 24 when the implant is radiographically viewed from the posterior side of the implant. When the implant is viewed radiographically from a lateral side, the anterior to posterior spaces S3, S4 between the support along the posterior sidewall, the support near a lateral aspect of the implant, and the support along the anterior sidewall indicate the rotational position of the implant. Embodiments of the invention may include charts or other indicators correlating spaces and patterns and rotational positioning.

Figure 29A:
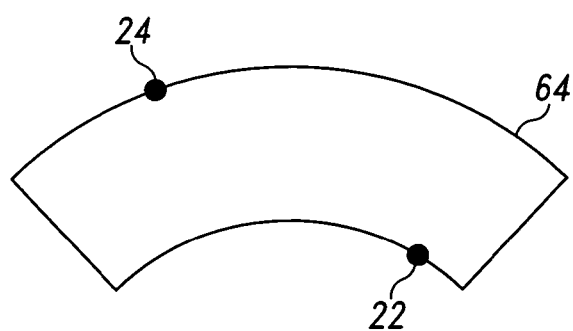
FIGS. 29A, 29B, and 29C are graphical representations of embodiments of an implant of the invention in plan (axial), side (lateral), and posterior views respectively.
Figure 29B:
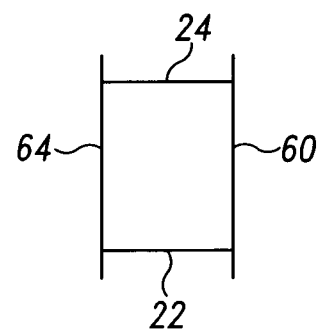
Figure 29C:
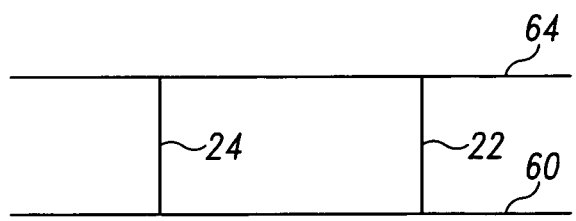

FIGS. 29A-29C illustrate an implant with a posterior support 22 along the posterior wall and an anterior support 24 along the anterior wall. When the implant is viewed radiographically from a posterior side, the lateral space between the posterior support 22 and the anterior support 24 indicates the rotational position of the implant. When the implant is viewed radiographically from a lateral side, the anterior to posterior space between the posterior support 22 and the anterior support 24 indicates the rotational position of the implant.

While the implants are intended primarily for use in spinal fusion, it is appreciated that they may be modified or adapted to receive fusion promoting substances and/or materials within them such as, but not limited to cancellous bone, bone derived products, chemotherapeutic agents, antimicrobial agents, or others. In some embodiments, the implants consists of materials such as, but not limited to, titanium and its alloys, ASTM material, cobalt chrome, tantalum, ceramic, polyether-ether-ketone (PEEK), various plastics, plastic composites, carbon fiber composites, coral, and can include artificial materials which are at least in part bioresorbable. The radiographic appearance of the structural materials employed in the implants are intended to be of varying nature such that optimal visualization of implant placement, implant-bone interfaces and/or bone ingrowth and through-growth can be achieved.

While the descriptions reveal various relationships, parallel or not, of upper to lower surfaces of the implants, it should be noted that deliberate angulation between surfaces relative to each other is possible. Subsequently, when implanted into the spine, such implants permit position of the adjacent vertebral bodies in angular relationship to each other to restore the natural curvature of the spine, such as lordosis for example. It should also be noted that significant variations in shape of the implants are possible including but not limited to: kidney shaped, rounded, wedge shaped, cylindrical, trapezoidal, rectangular, oblong, oval.

Outer surfaces may contain threading or particular unevenness for improved insertion or anchorage into surrounding tissues or bone. In any of the embodiments of the present invention, the implants may include, be made of, treated, coated, filled, used in combination with, or have a hollow space or opening for containing artificial or naturally occurring materials and/or substances suitable for implantation in the human spine. These materials, and/or substances, may include any source of osteogenesis, bone growth promoting materials, bone, bone derived substances or products, demineralized bone matrix, mineralizing proteins, ossifying proteins, bone morphogenetic proteins, hydroxyapatite, genes coding for the production of bone, and bone including, but not limited to, cortical bone, antibiotics, cancer treating substances, infection treating substances or other disease treating substances. The implant can include, at least in part materials that are bioabsorbable and/or resorbable in the body. The implants of the present invention can be formed of a porous material or can be formed of a material that intrinsically participates in the growth of bone between adjacent vertebral. At least a portion of the implant may be treated to promote bone ingrowth between the implant and the adjacent vertebral bodies.

The implant of the present invention may be used in combination with a spinal fixation device such as any device, regardless of material, that can be inserted into any portion of the spine, such as but not limited to interbody spinal implants, structural bone grafts, mesh, cages, spacers, staples, bone screws, plates, rods, tethers of synthetic material or wires, or other spinal fixation instrumentation. While the invention has been described with reference to particular embodiments, it will be appreciated by those of ordinary skill in the art that various modifications can be made to the invention itself without departing from the spirit and scope thereof. All changes and modifications that are within the spirit of the invention are hereby anticipated and claimed.

A method under the invention includes implanting an intervertebral implant from a transforaminal surgical approach. An implant consistent with the transforaminal implants disclosed herein is provided to carry out the method. One such implant has a generally convex anterior sidewall, a generally concave posterior sidewall, a superior portion for engaging a superior vertebral body, an inferior portion for engaging an inferior vertebral body, a proximal end between the anterior and posterior sidewalls made at least in part of a radiolucent material, and a distal end between the anterior and posterior sidewalls and generally opposite from the proximal end. The distal end is made at least in part of a radiolucent material.

The method further includes radiographically observing placement of the implant between the superior and inferior vertebral bodies. This observation may be accomplished through one or more of the proximal and distal ends, the anterior sidewall, and the posterior sidewall of the implant. Other viewing orientations oblique to those listed here would also be available in some embodiments. Effective radiographic viewing is enabled by embodiments of the invention that provide medial-lateral and anterior-posterior viewing paths. However, selective placement of radio-opaque materials that both structurally support and notify a surgeon of implant orientation are present in some embodiments of the invention in combination with these viewing paths.

Radiographically observing placement of the implant may include observing relative alignment of two or more supports extending between the superior and inferior portions of the implant. By observing alignment of two or more supports, a surgeon may make corrections to the alignment of the device.

The method may also include radiographically observing bone growth between the superior and inferior vertebral bodies through one or more of the proximal and distal ends, the anterior sidewall, and the posterior sidewall. Observation of bone growth is enhanced by the provision of viewing paths provided through an implant that only include bone growth volumes and radiolucent materials.

A method of assembling a transforaminal intervertebral implant includes providing a body with a generally convex anterior sidewall, a generally concave posterior sidewall, a superior portion for engaging a superior vertebral body, and an inferior portion for engaging an inferior vertebral body. The body in some embodiments is made from a radio-opaque material such as titanium. The body may also be made of any material that provides at least some radiographic signature.

The method further includes applying a distal end between the anterior and posterior sidewalls. The distal end of the embodiment has less of a radiographic signature than the body. As used herein, applying the distal end between the anterior and posterior sidewalls may include adding the distal end to the body to become a part of one or both of the anterior and posterior sidewalls.

Applying the distal end may be accomplished in various ways. The distal end may be formed around at least a portion of the body. To accomplish this, the material of the distal end may be cast, injected, or molded directly around at least a portion of the body. The body may be included as a part of a mold or cast, or encapsulated within a mold or cast for application to the distal end.

Applying the distal end may also include interconnecting a material with at least a portion of the body. Interconnecting may also include casting, injecting, or molding material to the body, but without encapsulating the body. Interconnecting material may also involve forming a distal end completely separately from the body by milling, casting, forming, injecting, or molding. After the distal end is formed, it may then be applied to the body by any method of adhesion, interdigitation, or interconnection. In some embodiments, interconnecting may be accomplished by snapping the material of the distal end to the body.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An intervertebral implant comprising:
   a generally convex anterior sidewall defined by an anterior support member connected to a first superior support plate for engaging a superior vertebral body and a first inferior support plate for engaging an inferior vertebral body;
   a generally concave posterior sidewall defined by a posterior support member connected to a second superior support plate for engaging the superior vertebral body and a second inferior support plate for engaging the inferior vertebral body;
   a proximal end between the anterior and posterior sidewalls, wherein the proximal end includes a first superior portion connecting the first superior support plate of the convex anterior sidewall to the second superior support plate of the concave posterior sidewall and a first inferior portion connecting the first inferior support plate of the convex anterior sidewall to the second inferior support plate of the concave posterior sidewall, wherein a first end opening is defined between the first superior portion and the first inferior portion;
   a distal end between the anterior and posterior sidewalls and generally opposite from the proximal end, wherein the distal end includes a second superior portion connecting the first superior support plate of the convex anterior sidewall to the second superior support plate of the concave posterior sidewall and a second inferior portion connecting the first inferior support plate of the convex anterior sidewall to the second inferior support plate of the concave posterior sidewall, wherein a second end opening is defined between the second superior portion and the second inferior portion;
   a first lateral block configured to be removably inserted into the first end opening defined by the proximal end; and
   a second lateral block configured to be removably inserted into the second end opening defined the distal end.

2. The intervertebral implant of claim 1 wherein the implant includes a first material with a detectable radiographic signature and a second material with a radiographic signature different than the radiographic signature of the first material.

3. The intervertebral implant of claim 2 wherein the first and second lateral blocks are manufactured by the second material.

4. The intervertebral implant of claim 1 wherein at least a portion of the distal end has a reduced height to facilitate insertion of the implant between vertebral bodies.

5. The intervertebral implant of claim 1 wherein an upper portion of the first and second superior support plates include a bone engaging surface.

6. The intervertebral implant of claim 1 wherein a lower portion of the first and second inferior support plates include a bone engaging surface.

7. The intervertebral implant of claim 1 wherein an upper portion of the first and second superior support plates and a lower portion of the first and second inferior support plates include a bone engaging surface.

8. The intervertebral implant of claim 1 wherein an upper portion of the first and second superior support plates, a lower portion of the first and second inferior support plates, an upper surface of the first and second superior portions, and a lower surface of the first and second inferior portions include a bone engaging surface.

9. The intervertebral implant of claim 1 wherein the first and second lateral blocks include an upper ridge configured to engage an upper interior edge defined by the first superior portion and the second superior portion.

10. The intervertebral implant of claim 1 in combination with a bone growth or bone healing promoting substance.

11. An intervertebral implant comprising:
    a body defined by a convex anterior sidewall and a concave posterior sidewall, wherein each respective sidewall has a superior support plate and an inferior support plate integrally connected with one another by a support member centrally located on the convex anterior sidewall and the concave posterior sidewall running along a vertical axis, wherein the superior support plates of the convex anterior sidewall and concave posterior sidewall are connected to each other at opposing superior ends and the inferior support plates of the convex anterior sidewall and concave posterior sidewall are connected to each other at opposing inferior ends, wherein the superior opposing ends, the superior support plates, the inferior opposing ends, and the inferior support plates define a central cavity in the body, wherein a proximal end of the body defines a proximal end opening into the central cavity and a distal end of the body defines a distal end opening into the central cavity;

a first lateral block configured to be removably inserted into the distal end opening of the body and into the central cavity; and a second lateral block configured to be removably inserted into the proximal end opening of the body and into the central cavity.

12. The intervertebral implant of claim 11 wherein the superior support plates and inferior support plates are separated from one another by the central void by the respective support members.

13. The intervertebral implant of claim 11 wherein the implant includes a first material with a detectable radiographic signature and a second material with a radiographic signature different than the radiographic signature of the first material.

14. The intervertebral implant of claim 13 wherein the first lateral block and second lateral block is manufactured by the second material.

15. The intervertebral implant of claim 11 wherein an upper surface of the superior support plates include a bone engaging surface.

16. The intervertebral implant of claim 11 wherein a lower surface of the inferior support plates include a bone engaging surface.

17. The intervertebral implant of claim 11 wherein the first and second lateral blocks include a ridge sized and configured to engage an inside edge of the opposing superior ends.

18. The intervertebral implant of claim 17 wherein the ridge has a generally semi-circular shape.

19. The intervertebral implant of claim 11 wherein the first and second lateral blocks are positioned in at least a portion of the central cavity through gaps between the superior and inferior support plates defined by the support members.

20. An intervertebral implant comprising:

a superior support plate defined by a first convex anterior support plate and a first concave posterior support plate connected at opposing ends thereby defining a first opening into an interior space;

an inferior support plate defined by a second convex anterior support plate and a second concave posterior support plate connected at opposing ends thereby defining a second opening into the interior space;

an anterior support member positioned between the first convex anterior support plate and the second convex anterior support plate along a central horizontal axis of the first and second convex anterior support plates thereby defining third and fourth frontal end openings into the interior space;

a posterior support member positioned between the first concave posterior support plate and the second concave posterior support plate along the central horizontal axis of the first and second concave posterior support plates thereby defining fifth and sixth rear end openings into the interior space; and a first lateral block configured to be removably inserted into a respective opposing end of the superior and inferior support plates.

21. The intervertebral implant of claim 20 wherein the superior and inferior support plates and the anterior and posterior support members comprise a first material with a detectable radiographic signature and the first lateral block comprises a second material with a radiographic signature different than the radiographic signature of the first material.

22. The intervertebral implant of claim 20 wherein an upper surface of the superior support plate includes a bone engaging surface.

23. The intervertebral implant of claim 20 wherein a lower surface of the inferior support plate includes a bone engaging surface.

24. The intervertebral implant of claim 20 wherein the first lateral block includes a curved ridge on an upper end surface of the first lateral block configured to engage an inside curved surface of the opposing end of a respective superior support plate.

25. The intervertebral implant of claim 20 further comprising a second lateral block configured to be removably inserted into the other respective opposing end of the superior and inferior support plates.

26. The intervertebral implant of claim 20 wherein the opposing ends of the superior support plate have an upper surface that includes a bone engaging surface.

27. The intervertebral implant of claim 26 wherein an upper surface of the superior support plate includes a bone engaging surface.

28. The intervertebral implant of claim 27 wherein the opposing ends of the inferior support plate have a lower surface that includes a bone engaging surface.

29. The intervertebral implant of claim 28 wherein a lower surface of the inferior support plate includes a bone engaging surface.

* * * * *